US011896738B2

(12) United States Patent
Bierman

(10) Patent No.: US 11,896,738 B2
(45) Date of Patent: Feb. 13, 2024

(54) BIOMIMETIC ELECTRICALLY CONDUCTIVE HYALURONIC ACID-BASED HYDROGELS

(71) Applicant: THE REGENTS OF THE UNIVERSITY OF CALIFORNIA, Oakland, CA (US)

(72) Inventor: Rebecca Bierman, Santa Clarita, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 255 days.

(21) Appl. No.: 17/198,211

(22) Filed: Mar. 10, 2021

(65) Prior Publication Data
US 2021/0283312 A1    Sep. 16, 2021

Related U.S. Application Data

(60) Provisional application No. 62/988,879, filed on Mar. 12, 2020.

(51) Int. Cl.
| | | |
|---|---|---|
| *A61L 27/52* | (2006.01) | |
| *A61L 27/44* | (2006.01) | |
| *A61L 27/34* | (2006.01) | |
| *C08K 3/04* | (2006.01) | |
| *A61N 1/05* | (2006.01) | |
| *C08K 7/06* | (2006.01) | |
| *C08J 3/075* | (2006.01) | |
| *A61L 27/38* | (2006.01) | |
| *C08K 7/24* | (2006.01) | |

(52) U.S. Cl.
CPC ............... *A61L 27/52* (2013.01); *A61L 27/34* (2013.01); *A61L 27/3834* (2013.01); *A61L 27/3878* (2013.01); *A61L 27/443* (2013.01); *A61N 1/0551* (2013.01); *C08J 3/075* (2013.01); *C08K 3/042* (2017.05); *A61L 2400/12* (2013.01); *A61L 2400/18* (2013.01); *C08J 2305/08* (2013.01); *C08K 7/06* (2013.01); *C08K 7/24* (2013.01); *C08K 2201/001* (2013.01)

(58) Field of Classification Search
None
See application file for complete search history.

(56) References Cited

U.S. PATENT DOCUMENTS

| | | | |
|---|---|---|---|
| 9,283,283 | B2 | 3/2016 | Giammona et al. |
| 9,738,527 | B2 | 8/2017 | Li et al. |
| 9,994,812 | B2 | 6/2018 | Kim et al. |
| 10,682,079 | B2 | 6/2020 | Joseph et al. |
| 2010/0144904 | A1* | 6/2010 | Wang ..................... C08K 3/042 516/98 |
| 2011/0021899 | A1* | 1/2011 | Arps ...................... A61N 1/375 252/511 |
| 2011/0307042 | A1* | 12/2011 | DeCarmine .......... A61N 1/0553 29/841 |
| 2013/0230496 | A1 | 9/2013 | Mohapatra et al. |
| 2018/0151885 | A1* | 5/2018 | Bosnyak ............... H01M 4/625 |

FOREIGN PATENT DOCUMENTS

CN        104725657 A  *  6/2015

OTHER PUBLICATIONS

Bao et al. Biomaterials 2017 122:63-71 (Year: 2017).*
Bierman Hyaluronic Acid-based Hydrogels as an In Vitro Approach to Neural Stem/Progenitor Cell Differentiation 2018 (Year: 2018).*
Yang et al. Biomaterials Research 2016 20:31:1-7 (Year: 2016).*
Wang et al. RSC Advanced 2016 6:88411-88416 (Year: 2016).*
Omid Akhavan et al., Rolled graphene oxide foams as three-dimensional scaffolds for growth of neural fibers using electrical stimulation of stem cells, Carbon 97 (2016) 71-77.
Chih-Wei Chang et al., Design and Fabrication of a Multi-electrode Array for Spinal Cord Epidural Stimulation, IEEE (2014), 6834-6837.
Biswadeep Chaudhuri et al., Biocompatibility of electrospun graphene oxide-poly(ε-caprolactone) fibrous scaffolds with human cord blood mesenchymal stem cells derived skeletal myoblast, Materials Letters, 126 (2014) 109-112.
Courtney M. Dumont et al., Aligned hydrogel tubes guide regeneration following spinal cord injury, Acta Biomaterialia (2019), doi: https://doi.org/10.1016/j.actbio.2018.12.052.
William S. Hummers et al., Preparation of Graphitic Oxide, [Contribution from the Baroid Division, National Lead Company], Mar. 20, 1958, (1page); https://pubs.acs.org/sharingguidelines for options on how to legitimately share published articles.
Michele Iafisco et al., Electrospun Collagen Mimicking the Reconstituted Extracellular Matrix Improves Osteoblastic Differentiation Onto Titanium Surfaces, Journal of Nanoscience and Nanotechnology, vol. 13, 4720-4726, 2013.
Zin Z Khaing et al., High molecular weight hyaluronic acid limits astrocyte activation and scar formation after spinal cord injury, J. Neural Eng. 8 (2011) 046033 (12pp), doi:10.1088/1741-2560/8/4/046033.
Tae-Hyung Kim et al., Graphene-Based Materials for Stem Cell Applications, Materials 2015, 8, 8674-8690; doi:10.3390/ma8125481, www.mdpi.com/journal/materials.

(Continued)

*Primary Examiner* — Melissa S Mercier
*Assistant Examiner* — Caralynne E Helm
(74) *Attorney, Agent, or Firm* — VISTA IP LAW GROUP LLP

(57) ABSTRACT

An electrically conductive hyaluronic acid-based hydrogel is disclosed that is a crosslinked porous scaffold having a graphene-based material encapsulated or in contact within the porous scaffold. The graphene-based material includes one or more of graphene oxide foam, reduced graphene oxide foam, nanoplatelets, nanoparticles, or fibers. The porous scaffold may be formed over an implanted bioelectronic device such as a microelectrode array having a plurality of electrodes. The porous scaffold may also be used to control the differentiation of cells including Neural Stem/Progenitor Cells (NS/PCs).

7 Claims, 11 Drawing Sheets

(56) References Cited

OTHER PUBLICATIONS

Eric Krueger et al., Graphene Foam as a three-dimensional Platform for Myotube Growth, ACS Biomater Sci Eng. Aug. 8, 2016; 2(8): 1234-1241. doi: 10.1021/acsbiomaterials.6b00139.

Ning Li et al., Three-dimensional graphene foam as a biocompatible and conductive scaffold for neural stem cells, Scientific Reports, 3,1604, DOI:10.1038/srep01604.

Chien-Min Lin, et al., Hyaluronic acid inhibits the glial scar formation after brain damage with tissue loss in rats, Surgical Neurology 72 (2009) S2:50-S2:54.

Chien-Chi Lin et al., Thiol-norbornene photo-click hydrogels for tissue engineering applications, J Appl Polym Sci. Feb. 20, 2015; 132(8): doi:10.1002/app.41563.

Costanza Martelli et al., Graphene-Induced Transdifferentiation of Cancer Stem Cells as a Therapeutic Strategy against Glioblastoma, ACS Biomater. Sci. Eng. 2020, 6, 3258-3269.

Victoria G. Muir et al., Chemically Modified Biopolymers for the Formation of Biomedical Hydrogels, https://dx.doi.org/10.1021/acs.chemrev.0c00923.

Mohamad Pezeshki-Modaress et al., Gelatin-GAG electrospun nanofibrous scaffold for skin tissue engineering: Fabrication and modeling of process parameters, Materials Science and Engineering C 48 (2015) 704-712.

Sandra M. Holley et al., Peptide-modified, hyaluronic acid-based hydrogels as a 3D culture platform for neural stem/progenitor cell engineering, J Biomed Mater Res Part A. 2019:9999A:1-15.

M. C. Serrano et al., 3D free-standing porous scaffolds made of graphene oxide as substrates for neural cell growth, J. Mater. Chem. B, 2014, 2, 5698-5706.

Shreyas Shah et al., Guiding Stem Cell Differentiation into Oligodendrocytes Using Graphene-Nanofiber Scaffolds, Adv Mater. Jun. 11, 2014; 26(22): 3673-3680. doi:10.1002/adma.201400523.

Jianfeng Shen et al., Layer-by-Layer Self-Assembly of Graphene Nanoplatelets, Langmuir 2009, 25(11),6122-6128.

Jisoo Shin et al., Three-Dimensional Electroconductive Hyaluronic Acid Hydrogels Incorporated with Carbon Nanotubes and Polypyrrole by Catechol-Mediated Dispersion Enhance Neurogenesis of Human Neural Stem Cells, Biomacromolecules 2017, 18, 3060-3072.

S. Van Vlierberghe et al., Surface Modification of Polyimide Sheets for Regenerative Medicine Applications, Biomacromolecules 2010, 11, 2731-2739.

Xiaoyong Zhang et al., Distribution and biocompatibility studies of graphene oxide in mice after intravenous administration, Carbon, 49 (2011) 986-995.

\* cited by examiner

BIOMIMETIC ELECTRICALLY CONDUCTIVE HYALURONIC ACID-BASED HYDROGELS

RELATED APPLICATION

This application claims priority to U.S. Provisional Patent Application No. 62/988,879 filed on Mar. 12, 2020, which is hereby incorporated by reference. Priority is claimed pursuant to 35 U.S.C. § 119 and any other applicable statute.

TECHNICAL FIELD

The technical field generally relates to devices and methods that utilize biomimetic electrically conductive hydrogels. The technical field has particular suitability for coating for implanted bioelectronic devices used to, among other things, stimulate regions of the central nervous system (CNS). The technical field also relates to electrically conductive hydrogels for stem cell administrative therapy. The technical field further relates to electrically conductive hydrogels for use in in vitro cell culture platforms.

BACKGROUND

Spinal cord injuries (SCI) affect approximately 300,000 people currently living in the United States, the majority being aged 18-35 years. Many of these people live with paralysis for the remainder of their life along with the associated medical consequences, decreased quality of life and a lifetime of medical care ranging from $2.3-4.7 million depending on their site of injury. For these reasons there is a need for restorative rather than assistive care for spinal cord injury patients. Currently available invasive SCI treatments typically employ stem cell therapy (delivering cells that differentiate into the desired neural cells) and/or applied epidural stimulation of the patient's spinal cord in combination with physical rehabilitation and cognitive intent of movement. While these techniques have proven moderately successful for some patients, they can be improved upon to broaden their reach and impact. One major issue with all CNS implants is the risk of rejection by the body, which hinders the effectiveness of treatment.

When designing a treatment for spinal cord repair, the major considerations are how to supply the correct type and quantity of neural cells, safely introduce them to the injury site, and for stimulation devices, to create a sustainable interactive device to interface with the implanted endogenous environment. Current 2D and 3D in vitro culturing techniques can produce differentiated neural cells, but not necessarily very mature cells that can be applied to create functionalized networks within the SCI site. Another current issue is how to inject these cells safely to the injury site. Furthermore, currently used spinal microelectrode arrays which apply epidural stimulation to the spinal cord to initiate neural regeneration as well as deep brain stimulation electrodes and pacemaker leads have faced issues with reliability due to a fibrous tissue encapsulation of the device in mammals. The formation of fibrous or scar tissue surrounding these implantable electronic devices compromises signal transfer from the device to the surrounding environment.

SUMMARY

Hyaluronic acid (HA) is a ubiquitous glycosaminoglycan within the body as an integral component of the extracellular matrix. HA is biocompatible in that it does not elicit an immune response and in high molecular weight form has anti-inflammatory properties. HA has also been shown to counteract glial scar formation after central nervous system injury by decreasing the size of the scar and the overall number of astrocytic glial cells. HA-based hydrogels provide a 3D microenvironment for encapsulated cells that has shear thinning properties, which enables safe delivery of the cultured cells to the SCI site. The chemistry behind the hydrogels also provides for the ability to add integrin binding sites, peptides and other controllable factors to create a diverse combination of parameters. The tunability, biocompatibility and feasibility of HA-based hydrogels make them an attractive part of the electrically conductive cell-scaffold system.

In one embodiment, an electrically conductive scaffold system is disclosed that uses hyaluronic acid-based hydrogels in combination with a graphene-based material. In one embodiment the electrically conductive hyaluronic acid-based hydrogels are used to increase the efficacy of culturing cells such as Neural Stem/Progenitor Cells (NS/PCs) into functional neural networks within the hydrogel network. NS/PCs are pluripotent cells that can differentiate into neurons and glia. For SCI repair, it is important to produce populations of mature oligodendrocytes and neurons. These cells must be encapsulated, proliferated and differentiated reliably in vitro to create mature functional neural networks. When a SCI occurs, it consists of two stages, the primary and secondary injury. The glial scar formation is the most consequential aspect of the secondary injury and is characterized by astrocytes infiltrating the injury site, modulating the local microenvironment and likely preventing endogenous repair. Therefore, a spinal cord repair treatment should be two-fold, disrupting the glial scar formation and introducing a functional cell network/device interface to the affected area to initiate repair. A combinatorial graphene and electrically conductive hyaluronic acid-based hydrogel-based 3D microenvironment for NS/PC culture and subsequent delivery to the injury site can tackle both aspects.

In one particular application, the hyaluronic acid-based hydrogels are used to treat spinal cord injuries. The hyaluronic acid-based hydrogels may be natively injected or otherwise delivered to the target location in a mammal (e.g., a SCI site in some embodiments) to form a 3D porous scaffold in which forms the functional network for SCI repair. In other embodiments, the electrically conductive hyaluronic acid-based hydrogels are used as a coating or layer that is provided on implanted bioelectronic devices such as microelectrode arrays that are used to treat spinal cord injuries. In some embodiments, the electrically conductive hyaluronic acid-based hydrogels uniformly include graphene-based materials therein and are applied over the surface of the implanted bioelectronic devices. In other embodiments, the electrically conductive hyaluronic acid-based hydrogels may include a hydrogel that is punctuated with discrete regions or locations that contain the graphene-based material. For example, these regions may be formed in apertures or holes that overlie the individual electrically conductive electrodes of a microelectrode array. The apertures or holes are then filled with the graphene-based material and/or a hydrogel containing the same. In other embodiments, a non-conductive hyaluronic acid-based hydrogel is in contact with a base or substrate that is made from a graphene-based material e.g., fibers that form the base or substrate.

In one embodiment, the graphene-based material that is incorporated into the hyaluronic acid-based hydrogel is incorporated as a foam such as graphene oxide foam (GO foam) or reduced graphene oxide foam (rGO foam). The GO foam or rGO foam is mixed with hydrogel precursor materials prior to crosslinking and is encapsulated or otherwise entrained within the porous scaffold that is formed after crosslinking. In other embodiments, however, the GO foam is not reduced. These may have particular applications where electrical conductivity is not as desired but the chemical handles of the GO foam can otherwise be used for conjugation of desired molecules, proteins and the like. In another embodiment, electrospun graphene oxide fibers are integrated into the hydrogel or portions thereof. For example, graphene nanoparticles may be used to create a graphene oxide poly(ε-caprolactone) (GO-PCL) scaffold or fibers that is encapsulated within the hydrogel, used as a base or substrate beneath the hyaluronic acid-based hydrogel, coated onto the microelectrode array, or located within conductive apertures or holes located where the individual conductive electrodes are located in the microelectrode array. In another embodiment, graphene nanoplatelets (GNPs) are used. These may be integrated into the hydrogel or formed in layer-by-layer (LBL) films which can be used as a highly conductive substrate or base on which hyaluronic acid-based hydrogels are made. The layers can also be used within conductive apertures or holes located where the individual conductive electrodes are located in the microelectrode array.

The electrically conductive hyaluronic acid-based hydrogels may be used to treat other central nervous system (CNS) disorders/diseases beyond just SCI repair. For example, electrodes may be placed within the brain for deep brain stimulation. The electrically conductive hyaluronic acid-based hydrogels may be used in connection with electrodes and other implantable devices, such as pacemakers, that require the transmission or delivery of electrical signals to one or more body tissues. Additional tissue types besides CNS tissue may be treated including, but not limited to, peripheral nervous system (PNS) tissue, epithelial tissue, and muscle tissue.

In one embodiment, an electrically conductive hyaluronic acid-based hydrogel is formed as a crosslinked porous scaffold formed from hyaluronic acid and having a graphene-based material encapsulated or in contact within the porous scaffold. The hyaluronic acid may include thiolated hyaluronic acid or methacrylated hyaluronic acid depending on the synthesis protocol. The graphene-based material includes one or any combination of: graphene oxide foam, reduced graphene oxide foam, nanoplatelets, nanoparticles, or fibers.

In one embodiment, an electrically conductive hyaluronic acid-based hydrogel comprising a crosslinked porous scaffold formed from hyaluronic acid and having a graphene-based material encapsulated or in contact within the porous scaffold.

In another embodiment, implanted bioelectronic device comprising a plurality of electrodes, the device comprising a polymer coated body and a plurality of metallic electrodes, wherein an electrically conductive hyaluronic acid-based hydrogel crosslinked into a porous scaffold is adhered to the polymer coated body and wherein the porous scaffold contains a graphene-based material encapsulated in contact therein.

In another embodiment, a method of culturing cells comprising: providing an electrically conductive, crosslinked hyaluronic acid-based hydrogel that forms a porous scaffold having a graphene-based material encapsulated in contact within the porous scaffold; providing within, on, or adjacent to the porous scaffold; and applying electrical current through the porous scaffold.

BRIEF DESCRIPTION OF THE DRAWINGS

FIG. 11A shows the removal of two vertebrae (T11 and L3). FIG. 11B shows the remaining intermediate vertebrae and exposed access points on either side. FIG. 11C shows the implanted electrically conductive hyaluronic acid-based hydrogel coated microelectrode array aligned between L2 and S1 of the spinal cord to parallel the walking central pattern generator for stimulation protocols in a rat model.

DETAILED DESCRIPTION OF ILLUSTRATED EMBODIMENTS

Figure 1:
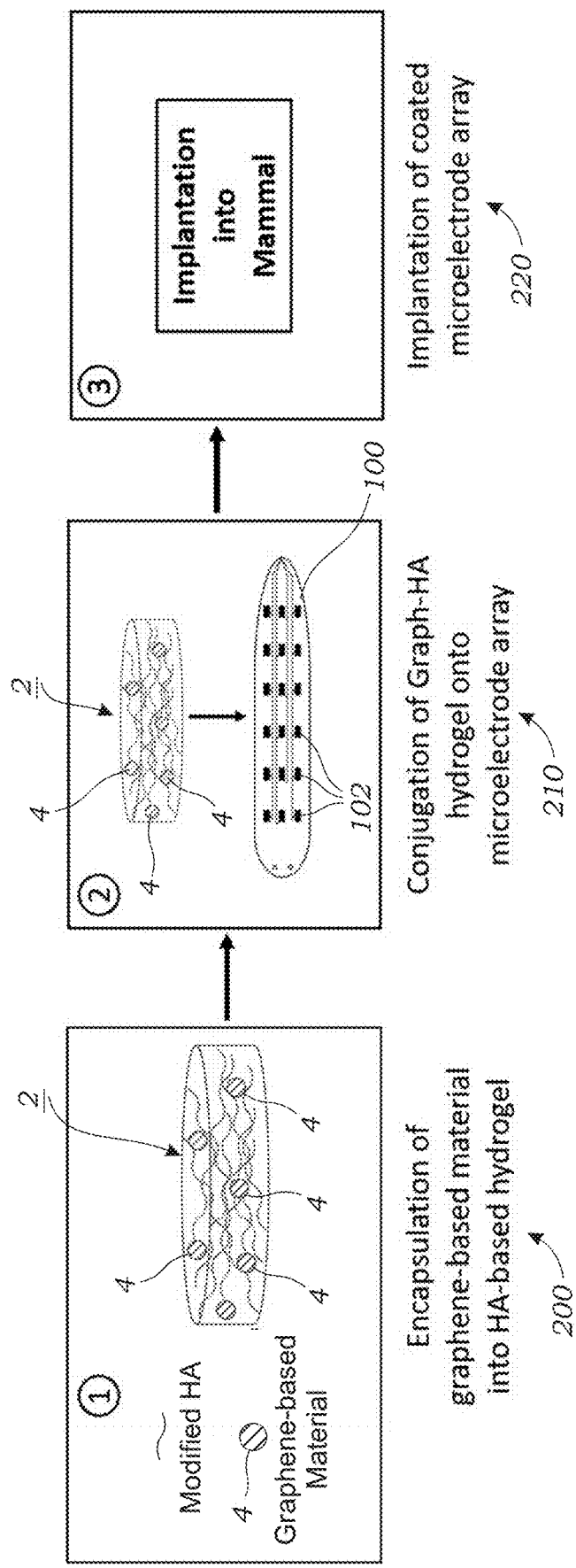
FIG. 1 schematically illustrates one embodiment of forming an electrically conductive hyaluronic acid-based (Graph-HA) hydrogel that conjugates this hydrogel to the polymer-based (e.g., polyimide) microelectrode array which is then implanted into a mammal.

FIG. 1A illustrates an electrically conductive hyaluronic acid-based hydrogel 2 according to one embodiment. The electrically conductive hyaluronic acid-based hydrogel 2 is crosslinked and includes one or more forms of a graphene-based material 4 that is disposed in the hyaluronic acid-based hydrogel 2. The graphene-based material 4 that is contained in the hyaluronic acid-based hydrogel 2 may, in one embodiment, be uniformly distributed through the hyaluronic acid-based hydrogel 2. In other embodiments, the graphene-based material 4 may be punctuated in different discrete regions of the electrically conductive hyaluronic acid-based hydrogel 2. In other embodiments, the graphene-based material 4 may be in contact with a non-electrically conductive hydrogel. The presence of the graphene-based material 4 imparts electrical conductivity properties to the hyaluronic acid-based hydrogel 2. The graphene-based material 4 may take one or more forms including, for example, graphene oxide (GO) (e.g., GO foam illustrated in FIGS. 5A and 6A), reduced graphene oxide (rGO) (e.g., reduced GO foam) illustrated in FIGS. 5B and 6B, graphene nanoplatelets (GNPs), which may also be reduced or not reduced, graphene nanoparticles, or graphene fibers. The electrically conductive hyaluronic acid-based hydrogel 2 is crosslinked with the graphene-based material 4 encapsulated or otherwise entrained within the three-dimensional structure or scaffold that is formed by the crosslinked hydrogel scaffold. The hyaluronic acid-based hydrogel 2 may be shaped into any number of different geometries or sizes. For example, a mold may be used to create final structures of the electrically conductive hyaluronic acid-based hydrogel 2 with the desired size and/or shape. In addition, the electrically conductive hyaluronic acid-based hydrogel 2 may be formed as a coating or layer over another substrate. This may be biological material or non-biological material. In some embodiments, the electrically conductive hyaluronic acid-based hydrogel 2 may be injected into living tissue where it may conform to tissue or other organs or fill voids or other spaces. The electrically conductive hyaluronic acid-based hydrogel 2 may optionally contain peptides bound thereto such as cellular adhesion proteins (e.g., RGD peptides) or therapeutic drugs.

The electrically conductive hyaluronic acid-based hydrogel 2 may be used to treat central nervous system tissue, specifically to interface with the brain and spinal cord tissue as a coating for epidural microelectrode arrays 100 and deep brain stimulation electrodes or as an injectable biomaterial for various CNS treatment applications. The electrically conductive hyaluronic acid-based hydrogel 2 may be used to treat peripheral nervous system (PNS) tissue, for instance, to interface with peripheral nerve cells for nerve graft applications. The electrically conductive hyaluronic acid-based hydrogel 2 may be used with epithelial tissue, specifically to interface with skin tissue in wound healing applications such as being incorporated into wound dressings. The electrically conductive hyaluronic acid-based hydrogel 2 may also be used with muscle tissue, for example, to interface with cardiac tissue as a coating for pacemaker leads or as an injectable biomaterial for cardiovascular applications.

In one particular application, the electrically conductive hyaluronic acid-based hydrogel 2 is used to treat spinal cord injuries. The electrically conductive hyaluronic acid-based hydrogel 2 may be natively injected (e.g., using a syringe or other delivery device) or otherwise delivered to the SCI site in some embodiments to form a 3D porous scaffold in which forms the functional network for SCI repair. The pre-polymer mixture (HA-SH) that is crosslinked to form the electrically conductive hyaluronic acid-based hydrogel 2 has shear-thinning properties in that it can readily be dispensed using a syringe as the application of pressure from a syringe barrel will fluidize the hydrogel 2 for delivery through the needle which then crosslinks in-situ. This may be accomplished by separating the pre-polymer components into separate delivery devices (or compartments of a single device) which are then immediately dispensed into the tissue (e.g., using a double-barrel syringe or the like). The pre-polymer components then mix to form the crosslinked electrically conductive hyaluronic acid-based hydrogel 2 within the body at the site of delivery or injection. For MeHA-based hydrogel 2, the pre-polymer mixture may be delivered to the desired site and UV radiation applied to initiate crosslinking. This may be done through a wand, flashlight, probe, catheter, or other working device that emits ultraviolet light.

Figure 2:
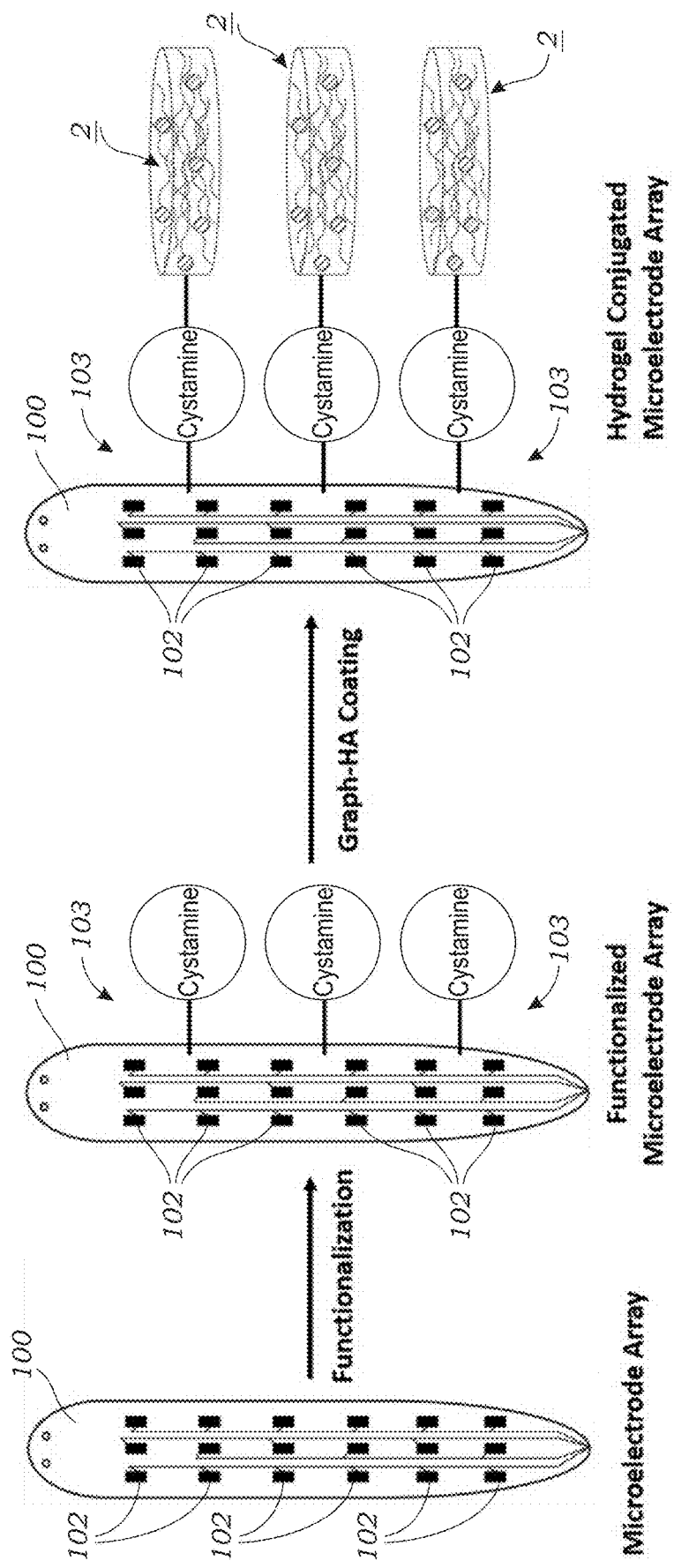
FIG. 2 schematically illustrates the process for conjugating or linking the Graph-HA hydrogel to the polyimide-based microelectrode array.

In other embodiments, such as illustrated in FIGS. 1, 2, 9B, 10B, the electrically conductive hyaluronic acid-based hydrogel 2 is used as a coating or layer that is provided on implanted bioelectronic devices such as microelectrode arrays 100 that are used, in one illustrative application, to treat spinal cord injuries. Individual electrodes 102 are located on the microelectrode array 100 device as seen in FIGS. 1 and 2. The electrically conductive hyaluronic acid-based hydrogel 2 may also be created as a substrate layer that is bonded or adhered to another surface.

The electrically conductive hyaluronic acid-based hydrogel 2 may, in some embodiments, be used as an electrically conductive biomaterial that functions or provides therapeutic benefits even without application of any external electrical field. For example, the electrically conductive hyaluronic acid-based hydrogel 2 may be an injectable therapeutic that can be used as a medium for injecting stem cells to the body of a mammal and then provide a local microenvironment that is conducive for healing, wherein the conductive nature of the hydrogel 2 can be advantageous in and of itself. For example, the electrically conductive hyaluronic acid-based hydrogel 2 may promote the proliferation, migration and differentiation of neural stem cells. The endogenous neural activity within the body can be conducted through the electrically conductive hyaluronic acid-based hydrogel 2; acting as a bridge across injured areas of the CNS/PNS tissue.

The electrically conductive hyaluronic acid-based hydrogel 2 may also be used as a research or investigational tool for in vitro applications. For example, the electrically conductive hyaluronic acid-based hydrogel 2 may serve as a platform for in vitro cell culture and/or a cell manufacturing platform. For example, the electrically conductive hyaluronic acid-based hydrogel 2 can be used to grow neural stem cells (or other cell types) and differentiate them into specific lineages of mature neural cells that can be tested solely in vitro or subsequently implanted into the body in a mature state and because of the shear thinning properties of the material survive the transplantation (e.g., platform for culturing cells). The electrically conductive hyaluronic acid-based hydrogel 2 may be used to create a 3D conductive biomaterial environment that can be used as a tool for recording signals from encapsulated cells to study their behavior within the conductive environment as well as in response to applied stimulation. This platform can also be used for drug testing in which specific drugs can be conjugated to the graphene-based material 4 or HA backbone and released according to specific timetables to study their efficacy against various encapsulated cell types.

FIG. 1 schematically illustrates one embodiment of forming an electrically conductive hyaluronic acid-based hydrogel 2 that first encapsulates a graphene-based material 4 into a hyaluronic acid (HA)-based hydrogel as seen in operation 200. This hyaluronic acid-based hydrogel 2 is then chemically bound to the functionalized polyimide microelectrode array 100 (FIG. 1) as seen in operation 210 which is then implanted into a mammal as seen in operation 220 of FIG. 1 (also seen in FIGS. 1A-11C). FIG. 2 illustrates the process for conjugating or linking the electrically conductive hyaluronic acid-based hydrogel 2 to the polyimide-based microelectrode array 100 according to one embodiment. The microelectrode array is functionalized with a cystamine-modified surface using, for example, cystamine and methanol tributylamine to produce a cystamine-modified surface 103. The hydrogel 2 then forms covalent bonds between the PEG-Mal of the electrically conductive hyaluronic acid-based hydrogel 2 and exposed thiol of the cystamine modified surface.

Two different methods may be used to functionalize the surface of the microelectrode array 100. A first method involves a cystamine functionalization method in which cystamine dihydrochloride and tributylamine were added to methanol and used to soak the array 100 overnight. The following day the array 100 was rinsed several times with deionized $H_2O$ and then placed in a solution of DTT and left for two hours at room temperature. The array 100 was then rinsed in deionized $H_2O$ several times again and dried overnight. The second method uses a TMSPMA functionalization method in which the array 100 is soaked in 2.75M NaOH solution overnight, rinsed the following day in deionized $H_2O$ and submerged in 98% TMSPMA overnight again at 80° C. The next day the array is washed in 200 proof Ethanol several times and dried overnight. MeHA solution was then prepared and photocrosslinked to each microelectrode array 100. While both methods described above may be used, the first method (cystamine method) led to stronger adherence of the electrically conductive hyaluronic acid-based hydrogel 2 to the microelectrode array 100.

Figure 3:
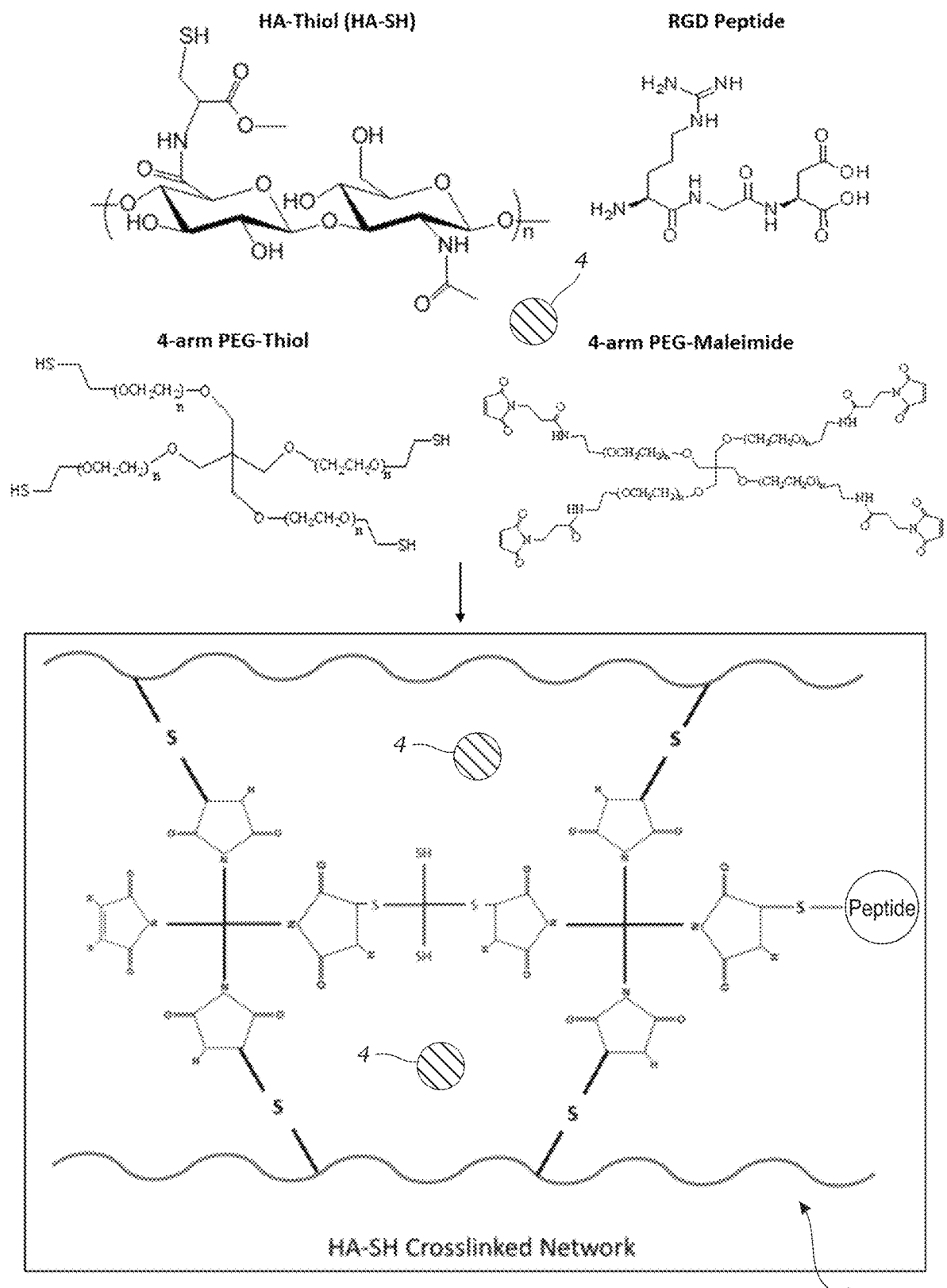
FIG. 3 illustrates one embodiment of a synthesis method used to make an electrically conductive hyaluronic acid-based hydrogel using thiolated hyaluronic acid (HA-SH) using Michael addition chemistry.

The electrically conductive hyaluronic acid-based hydrogel 2 may be formed using Michael addition chemistry. FIG. 3 illustrates one exemplary synthesis of electrically conductive hyaluronic acid-based hydrogel 2 using Michael addition chemistry. In this example, the hyaluronic acid-based hydrogel 2 is formed by a crosslinked porous scaffold formed by thiolated hyaluronic acid chains (HA-Thiol), multi-arm polyethylene glycol (PEG) thiol (PEG-SH) (4-arm example in FIG. 3), multi-arm polyethylene glycol maleimide (PEG-Mal) (4-arm example in FIG. 3) with one or more cell adhesion peptides (e.g., RGD peptide), and graphene-based material 4. In this example, the graphene-based material 4 is added to one or more of the pre-polymer solutions prior to crosslinking. The graphene-based material may include as noted herein, GO foam, rGO foam, graphene nanoplatelets, or graphene nanoparticles.

Figure 4:
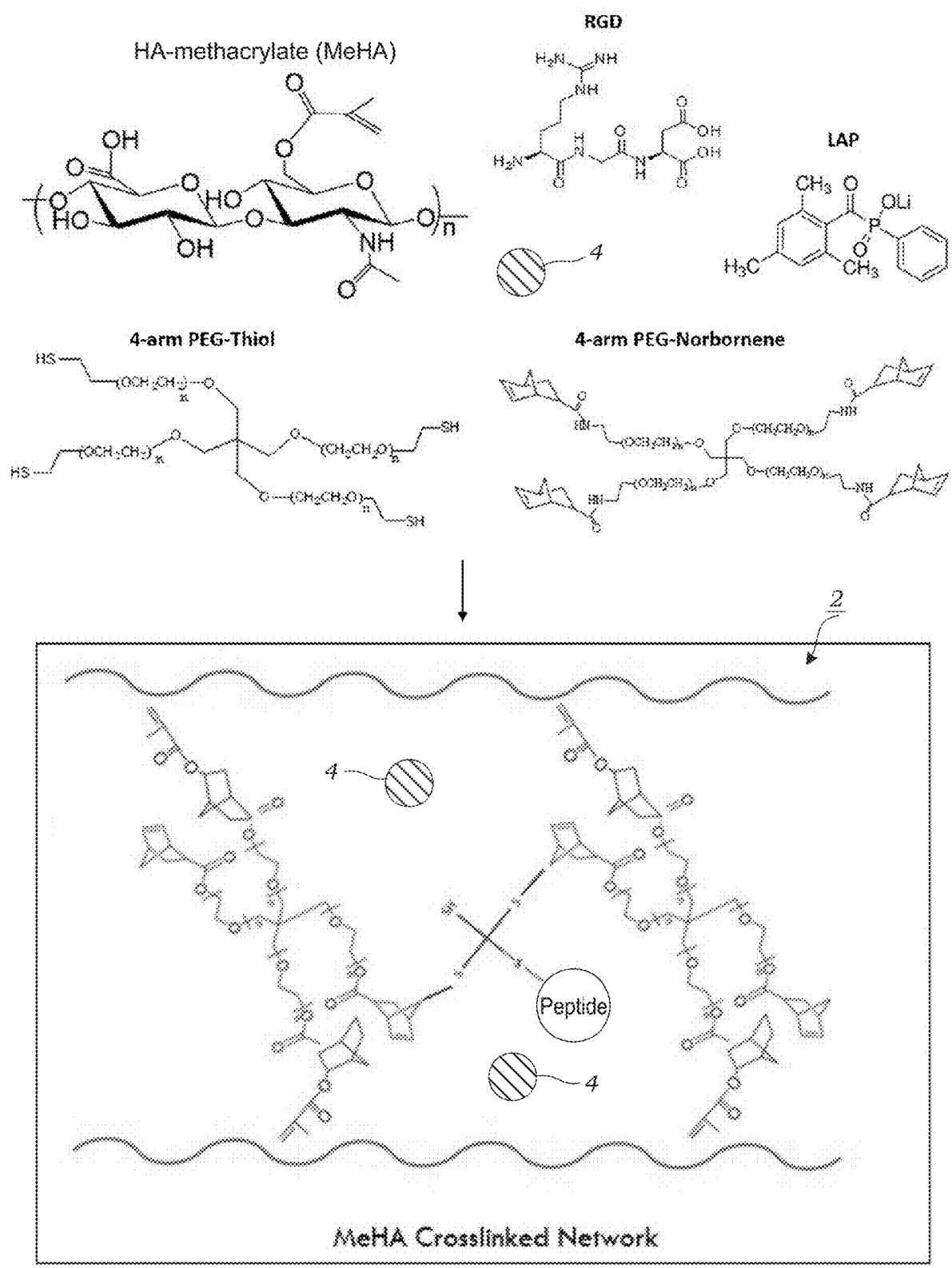
FIG. 4 illustrates another embodiment of a synthesis method used to make an electrically conductive hyaluronic acid-based hydrogel using methacrylated hyaluronic acid (MeHA) using photo-crosslinking.

FIG. 4 illustrates another exemplary synthesis of electrically conductive hyaluronic acid-based hydrogel 2. In this example, the electrically conductive hyaluronic acid-based hydrogel 2 is crosslinked using photochemistry. In this approach, methacrylated hyaluronic acid chains (MeHA), multi-arm polyethylene glycol (PEG) thiol (4-arm example in FIG. 4), multi-arm polyethylene glycol norbornene (PEG-Norb) (4-arm example in FIG. 4) with one or more cell adhesion peptides (e.g., RGD peptide), a photoinitiator (lithium phenyl-2,4,6-trimethylbenzoylphosphinate or (LAP) as one example) and graphene-based material 4 are subject to ultraviolet light irradiation to crosslink the electrically conductive hyaluronic acid-based hydrogel 2.

Figure 7A:
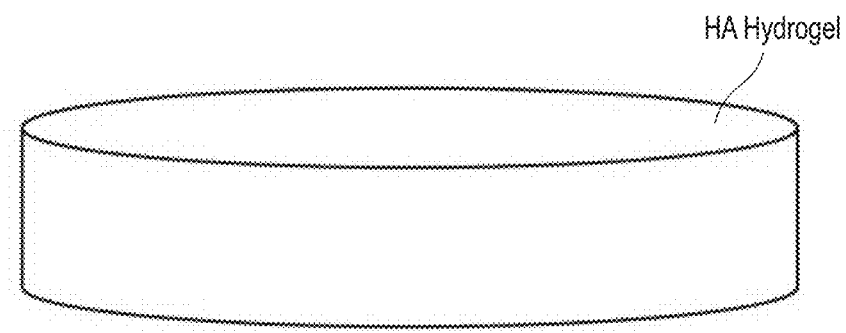
FIG. 7A illustrates a hyaluronic acid-based hydrogel is the shape of a disc or puck (4.5 mm diameter×2 mm height) with no graphene-based material contained therein.
Figure 7B:
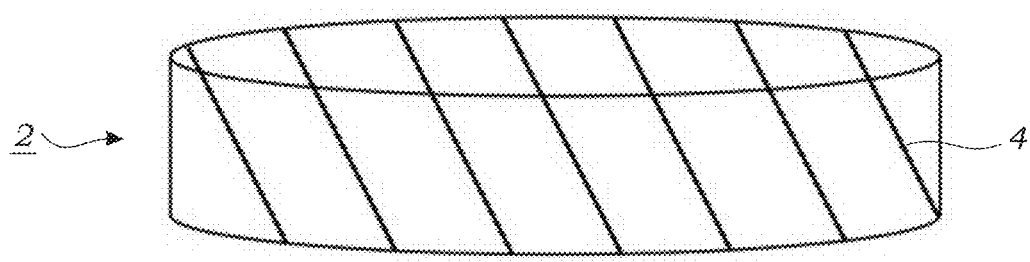
FIG. 7B illustrates an electrically conductive hyaluronic acid-based hydrogel is the shape of a disc or puck with rGO foam encapsulated or contained therein.
Figure 7C:
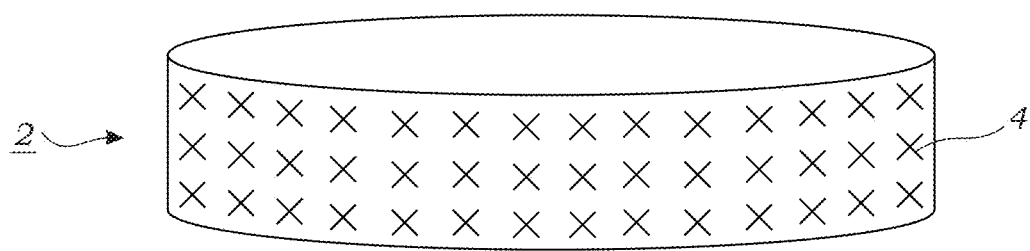
FIG. 7C illustrates an electrically conductive hyaluronic acid-based hydrogel is the shape of a disc or puck with electrospun GO-PCL fibers encapsulated or contained therein.
Figure 7D:
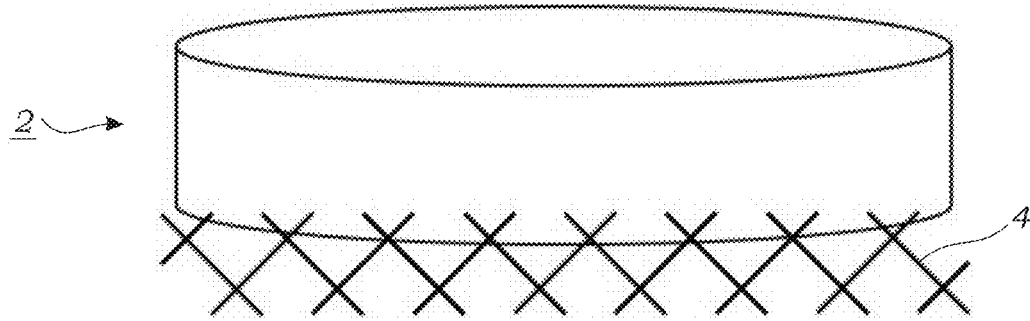
FIG. 7D illustrates an electrically conductive hyaluronic acid-based hydrogel that includes graphene nanoplatelets (GNPs) and electrospun GO-PCL fibers layered beneath the hydrogel scaffold.

FIGS. 7B-7D illustrate different types of electrically conductive hyaluronic acid-based hydrogels 2 compared to the standard HA-based hydrogel (4.5 mm diameter×2 mm height) with no graphene-based material 4 (FIG. 7A). FIG. 7A shows the HA-based hydrogel with no graphene-based material 4 contained therein. FIG. 7B illustrates rGO Foam as the graphene-based material 4 encapsulated within a hyaluronic acid-based hydrogel. FIG. 7C illustrates electrospun GO-PCL fibers encapsulated within a hyaluronic acid-based hydrogel. FIG. 7D illustrates graphene nanoplatelets (GNPs) and electrospun GO-PCL fibers can be a layered substrate located beneath a hyaluronic acid-based hydrogel.

Figure 8A:
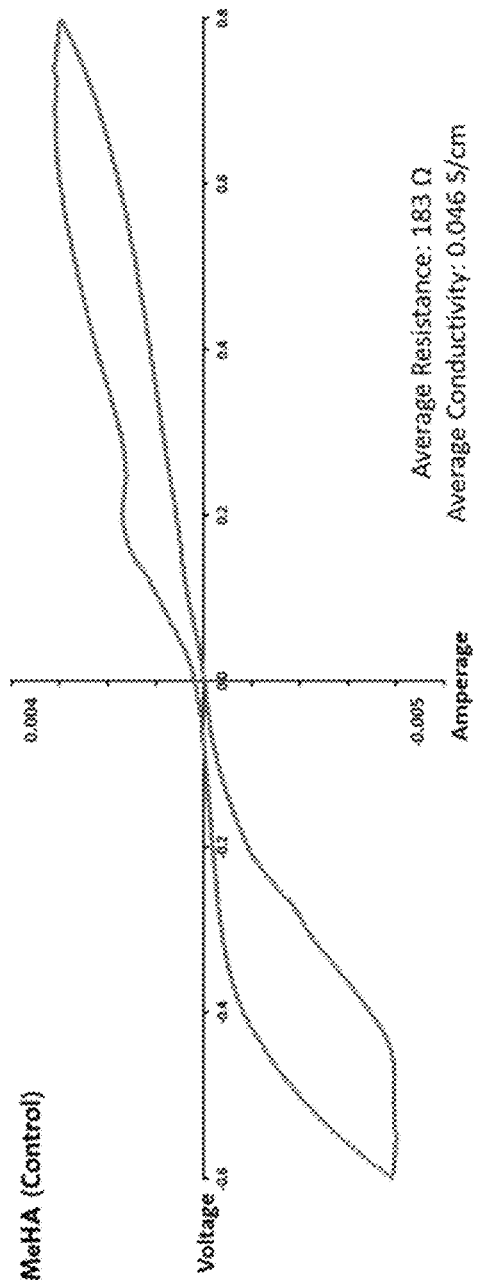
FIG. 8A illustrates a cyclic voltammogram of a hyaluronic acid-based hydrogel (methacrylated hyaluronic acid-based (MeHA)) with no graphene-based material contained therein. This serves as a control hydrogel.
Figure 8B:
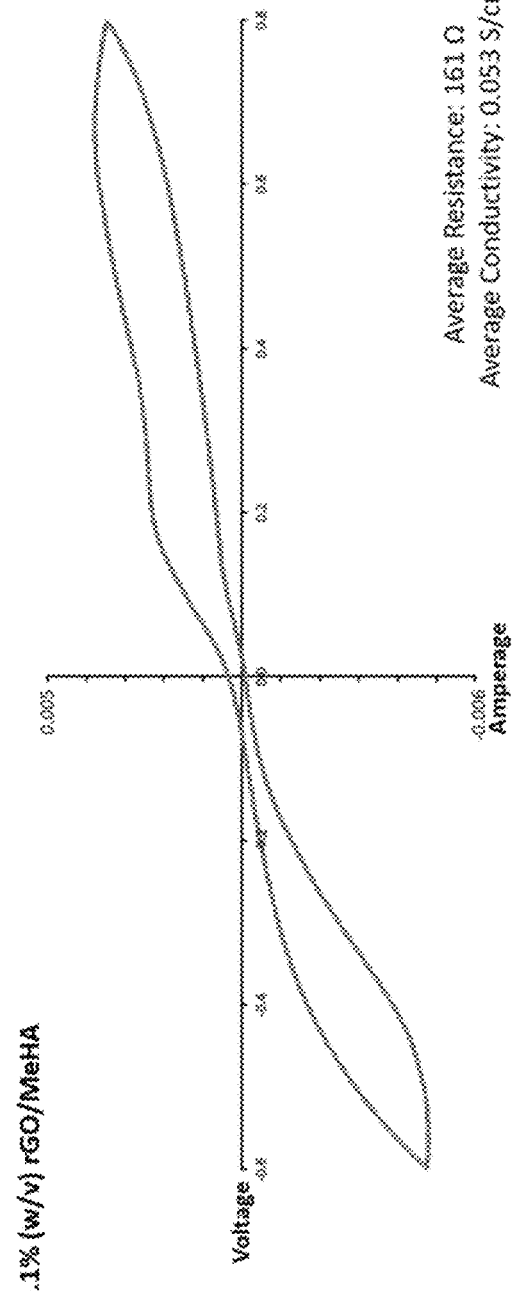
FIG. 8B illustrates a cyclic voltammogram of a hyaluronic acid-based hydrogel (methacrylated hyaluronic acid-based (MeHA)) with reduced graphene oxide (rGO) as the graphene-based material contained therein (0.1% (w/v) rGO/MeHA.
Figure 8C:
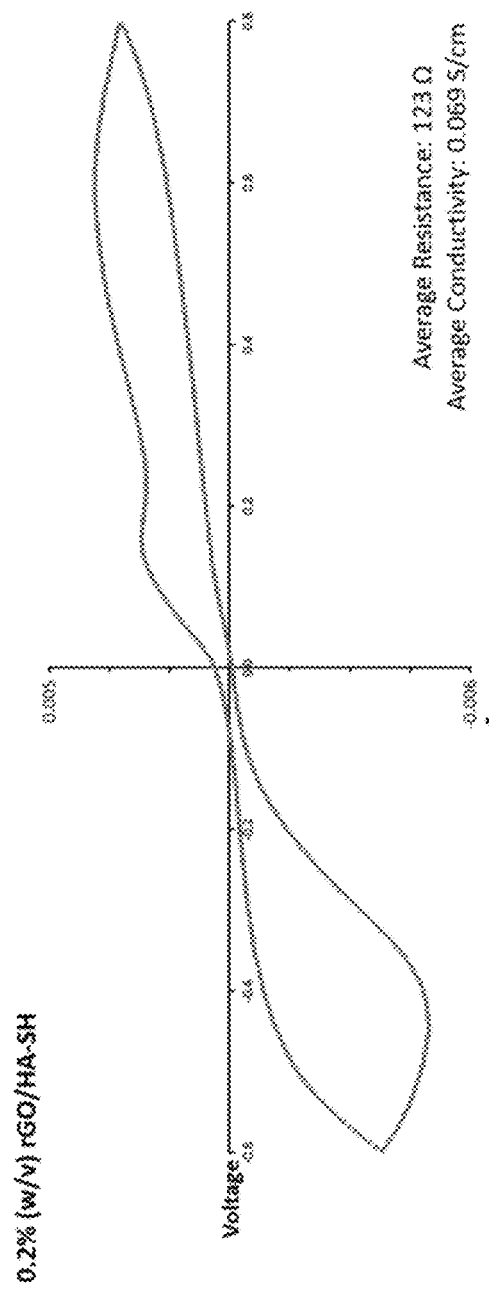
FIG. 8C illustrates a cyclic voltammogram of thiolated hyaluronic acid (HA-SH)-based hydrogel having reduced graphene oxide (rGO) as the graphene-based material contained therein (0.2% (w/v) rGO/HA-SH).
Figure 8D:
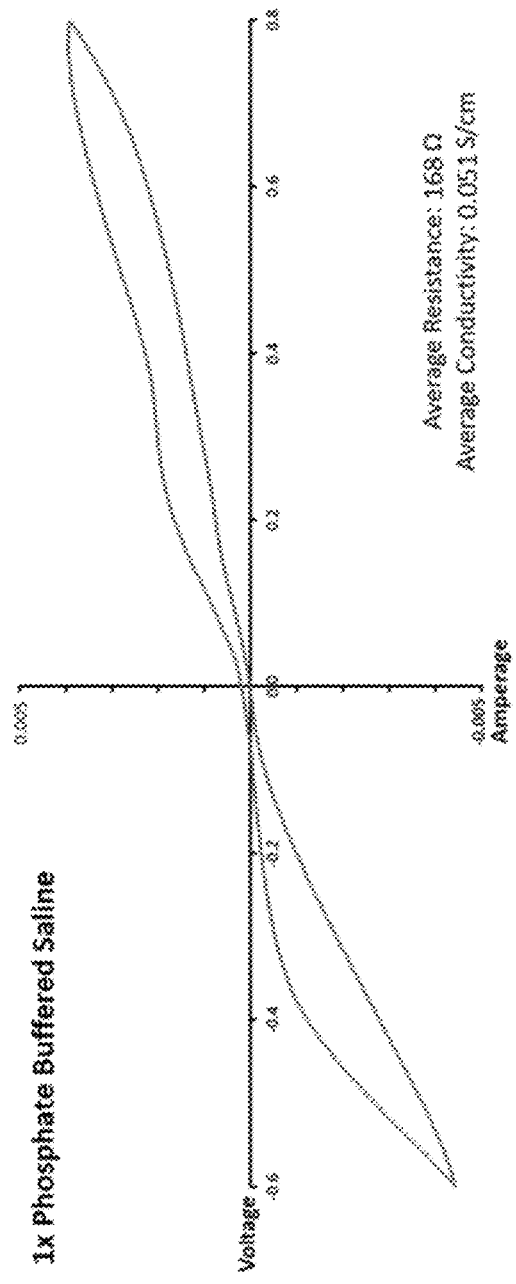
FIG. 8D illustrates the cyclic voltammogram of phosphate buffered saline (PBS).

FIGS. 8A-8C illustrate the cyclic voltammograms of different hyaluronic acid-based hydrogels and includes a control methacrylated hyaluronic acid-based (MeHA) hydrogel with no graphene-based material 4 contained therein (FIG. 8A) along with a MeHA-based hydrogel having reduced graphene oxide (rGO) as the graphene-based material 4 contained therein (0.1% (w/v) rGO/MeHA) (FIG. 8B). Hydrogels were evaluated for electrical properties using a PalmSens4 electrochemical system. Custom holders were designed and fabricated to accommodate hydrogels for testing. A three-probe system (working, counter and reference electrode) was used to scan voltages from (−0.6V-0.8V) with a step rate of 0.005 V and scan rate of 0.1V/s for a total of 5 scans. Scans were then averaged and plotted as cyclic voltammograms (FIGS. 8A-8C). Impedance and conductivity values were derived using a custom Matlab script. FIG. 8C illustrates the cyclic voltammogram of HA-Thiol (HA-SH)-based hydrogel having reduced graphene oxide (rGO) as the graphene-based material 4 contained therein (0.2% (w/v) rGO/HA-SH). It should be appreciated that the hyaluronic acid-based hydrogels may contain a graphene-based material 4 at higher ranges. For example, for electrically conductive hyaluronic acid-based hydrogels 2 made from HA-SH, graphene-based material 4 up to at least 3.8% (w/v) have been created. Higher loading of graphene-based material 4 beyond 3.8% is also possible. For Me-HA based electrically conductive hyaluronic acid-based hydrogels 2, the loading of graphene-based material 4 is lower, i.e., up to 1% (w/v) due to the photocrosslinking protocol.

These same hydrogels (control, MeHA, HA-SH) were subject to rheological characterization using a Discovery Hybrid Rheometer (DHR2) from TA instruments. Hydrogels were brought to room temperature and placed onto the bottom plate of the rheometer which was heated to 37° C. A parallel-plate geometry (8 mm) was used to perform an oscillation-frequency logarithmic sweep (0.1-10 Hz, 1.0% strain). Complex moduli were recorded and used to calculate averages and standard deviations of at least three technical repeats. Table 1 below illustrates the measured complex modulus (Pa) as well as the conductivity (from cyclic voltammetry).

TABLE 1

| Condition | Complex Modulus (Pa) | Conductivity (S/cm) |
| --- | --- | --- |
| Control 0.0% (w/v) in MeHA | 450 +/− 23 | 0.046 +/− 0.002 |
| rGO 0.1% (w/v) in MeHA | 454 +/− 32 | 0.053 +/− 0.006 |
| rGO 0.2% (w/v) in HA-SH | 520 +/− 40 | 0.069 +/− 0.004 |

Figure 9A:
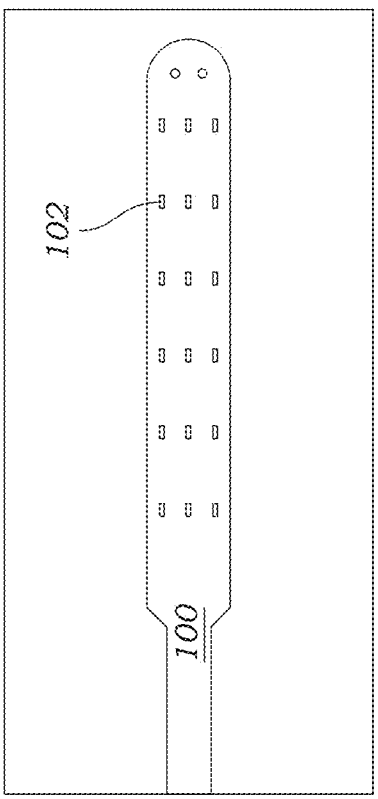
FIG. 9A illustrates a microscope image representation of a microelectrode array that is uncoated (no hydrogel scaffold located thereon). The array size is ~20 mm in length by ~2 mm width.
Figure 9B:
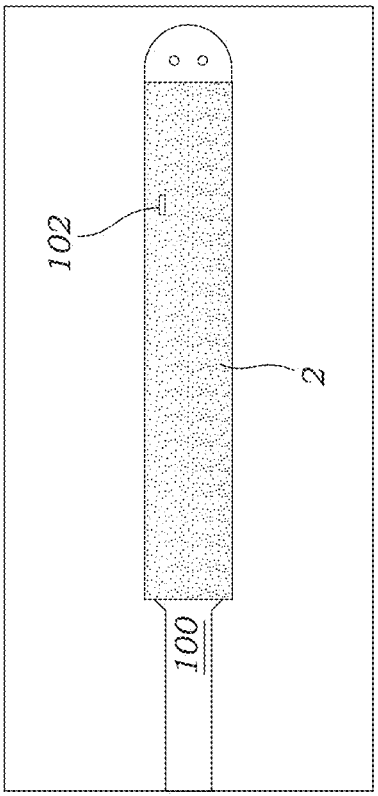
FIG. 9B illustrates a microscope image representation of a microelectrode array that is coated with an electrically conductive hyaluronic acid-based hydrogel.

FIG. 9A illustrates an example of a microelectrode array 100 that is uncoated (no hydrogel scaffold 2 located thereon). The array size is ~20 mm in length by ~2 mm width and includes rectangular electrodes 102 (0.2 mm×0.5 mm) populated on the body of the microelectrode array 100. FIG. 9B illustrates this microelectrode array 100 that is coated with an electrically conductive hyaluronic acid-based hydrogel 2. In this embodiment, the electrically conductive hyaluronic acid-based hydrogel 2 coats or overlays over the electrodes 102.

Figure 10A:
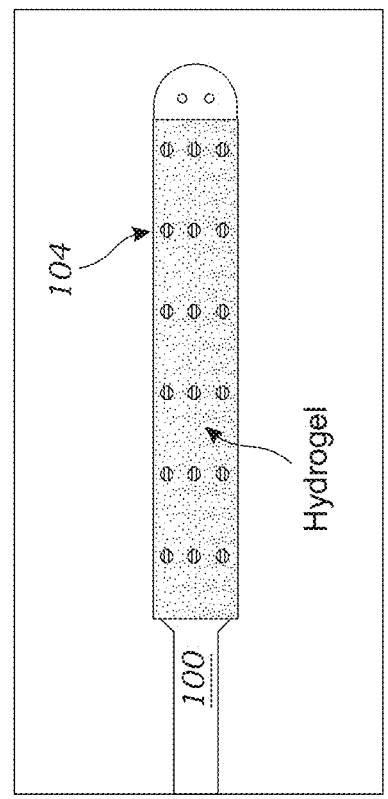
FIG. 10A illustrates a microscope image representation of a microelectrode array that is coated with a hydrogel (electrically non-conductive) with holes or apertures located at positions where the metal (e.g., platinum/iridium) electrodes are located.
Figure 10B:
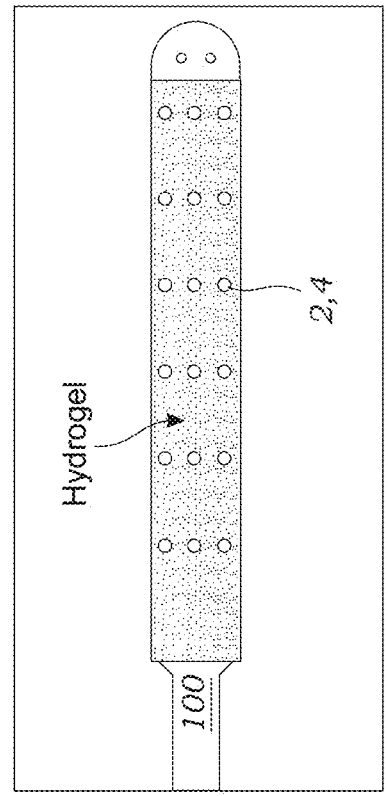
FIG. 10B illustrates the microelectrode array of FIG. 10 illustrating the holes or apertures filled with graphene-based material or an electrically conductive hyaluronic acid-based hydrogel.

FIG. 10A illustrates another embodiment of a microelectrode array 100 in which an electrically non-conductive hydrogel coating is applied to the microelectrode array 100 and forms holes or apertures 104 which are located at the areas where the electrodes 102 are located. The holes or apertures 104 are then filled with a graphene-based material 4 or an electrically conductive hyaluronic acid-based hydrogel 2. FIG. 10B illustrates the microelectrode array 100 of FIG. 10A with the holes or apertures 104 filled with an electrically conductive hyaluronic acid-based hydrogel 2 or graphene-based material 4.

Figures 11A, 11B, 11C:
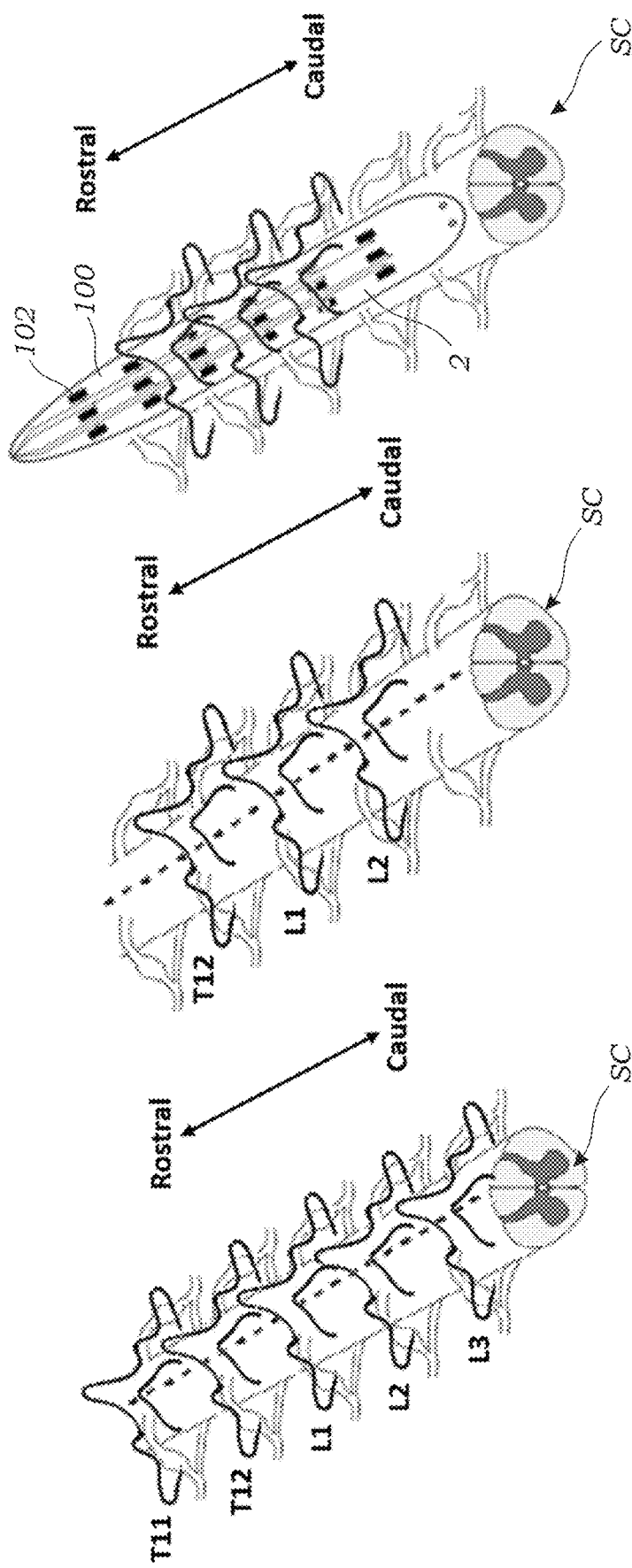
FIGS. 11A-11C illustrate an example of how a coated microelectrode array is implanted in a mammal (e.g., rat SCI models).

FIGS. 11A-11C illustrate how a microelectrode array 100 coated with an electrically conductive hyaluronic acid-based hydrogel 2 may be implanted in a mammal (e.g., rat SCI models). FIG. 11A shows the rat spinal cord SC and the removal of two vertebrae (T11 and L3). FIG. 11B shows the remaining intermediate vertebrae and exposed access points on either side. FIG. 11C shows the implanted electrically conductive hyaluronic acid-based hydrogel 2 coated microelectrode array 100 aligned between L2 and S1 of the spinal cord to parallel the walking central pattern generator for stimulation protocols. While a microelectrode array 100 is illustrated it should be appreciated that other biomedical devices with electrodes 102 may be coated with or otherwise in contact with an electrically conductive hyaluronic acid-based hydrogel 2.

Experiments were conducted in a rat model of implanting a microelectrode array 100 coated with a component of the electrically conductive hyaluronic acid-based hydrogel 2 (FIGS. 11A-11C). A microelectrode array 100 (Liu Lab, UCLA) was prepared by coating specific electrodes 102 with either silver epoxy only (Epoxy Technology, H20E) or silver epoxy with reduced graphene oxide foam (rGO, Kaner Lab UCLA), graphene oxide foam (GO, Kaner Lab UCLA), or graphene nanoplatelets (GNPs, Tokyo Chemical Industry Co., G0441). Graphene nanoplatelets are a particular type of nanoparticle that is made from short stacks of graphene sheets having a platelet shape. These are commercially available. The array 100 was then implanted epidurally onto a rat spinal cord under vertebral segments T12 to L2 and connected to a stimulator. Separately, bipolar wired electrodes were implanted bilaterally in the soleus and tibialis anterior muscles of the hind legs and connected to recording software. Stimulation was applied through paired electrodes of the microelectrode array 100 to test EMG responses from the control (silver epoxy only) and experimental (graphene-incorporated silver epoxy) conditions independently.

Electrodes 102 that were coated with rGO foam, or GNP-incorporated silver epoxy, demonstrated 10× better output voltage from the EMG recordings indicating improved conductivity of those electrodes 102 compared to the silver epoxy only group. Table 2 reproduced below illustrates the results.

TABLE 2

| Condition | Output Voltage |
| --- | --- |
| Control (silver epoxy) | 0.007 |
| GNPs in silver epoxy | 0.068 |
| rGO in silver epoxy | 0.069 |

Experiments were also conducted by encapsulating or seeding NS/PC cells into/onto electrically conductive hyaluronic acid-based hydrogels 2. Immortalized human neural stem/progenitor cells (NS/PCs, H9 ESCs, Life Technologies) were expanded and used for these experiments. NS/PCs were seeded initially onto a T75 flask that was prepared with a 1:100 solution of CELLstart™ (Life Technologies) in phosphate buffered saline (PBS) with $Ca^{2+}$/$Mg^{2+}$ (Genesee Scientific) in a humidified 37° C., 5% $CO_2$ incubator for at least 1 hour. The cells were then cultured in proliferation medium (48.5 mL Knockout Dulbecco's Modified Eagle's Medium F-12 (Genesee Scientific 1260-012), 0.2× Antibiotic-antimycotic (LifeTechnologies 1524XZ0062), 2 mM Glutamax™ (ThermoFisher 35050061), 20 ng/mL Epidermal Growth Factor (PeproTech AF-100-15), 20 ng/mL Basic Fibroblast Growth Factor (PeproTech 100-18B), and 2% StemPro® neural supplement (LifeTechnologies A1050901)) in a humidified 37° C., 5% $CO_2$ incubator. Culture medium was changed every 48 hours.

Before encapsulation, HA and crosslinker solutions were prepared according to the "Electrically conductive hyaluronic acid-based hydrogel (HA-SH)" operation described herein but under sterile conditions in a biosafety cabinet (BSC) with filtered solutions. Graphene solution was prepared and added to the HA solution to achieve a final concentration of 0.2% (w/v) rGO foam in each hydrogel. T75 flasks were passaged to prepare cell suspension for all hydrogel conditions and appropriate volumes of cell solution was added to the HA solutions to achieve a final concentration of 200 k cells in each hydrogel for encapsulation conditions. Alternatively, equal volumes of sterile PBS were added to HA solutions to be used for seeded hydrogel conditions and related cells were saved on ice. Press-to-seal silicone isolators (2 mm diameter by 1.6 mm deep, 20 μL volume, Grace BioLabs) were autoclaved, cooled and placed into the bottom of polystyrene petri dishes. 48-well plates were prepared with proliferation medium (500 μl per well). Next, the silicone molds were placed in a Petri dish and 20 μL of the HA solution (with cells for the encapsulation conditions and without cells for the seeded conditions) was added to each mold. Then the petri dish was placed in an incubator (37° C. 5% $CO_2$ 95% humidity) for 30 minutes. When the hydrogels 2 were fully formed, they were separated from the silicone molds and carefully transferred to the wells of a 48-well plate that were prepared with media. For the seeded conditions, before removing hydrogels 2 from the molds the top of the hydrogels 2 were scored in a crosshatch pattern with a sterilized razor blade and then seeded with 200 k NC/PCs per hydrogel 2. All hydrogels 2 were then stored in the incubator and maintained with fresh proliferation medium for the following ten days.

On day 10, hydrogels 2 were segregated into three conditions that received either 0V, 4V or 10V of applied stimulation. All equipment was sterilized or kept outside of the BSC during this procedure. Hydrogels 2, one at a time, were removed from the 48-well plate and laid atop electrodes 9 (anode) and 10 (cathode) of a microelectrode array 100 (Liu lab, UCLA). Bipolar stimulation was applied at a 0.4 Hz frequency with a 0.1 ms pulse width, for a 1-minute total stimulation period. Hydrogels 2 were then returned to their respective wells and maintained for an additional 4 days in proliferation medium, at which time they were observed and embedded for immunohistochemical analysis. Hydrogel conditions with NS/PCs seeded atop were compared for the different stimulation conditions. Conditions that received 4V or 10V showed greater cell aggregation and neurite formation compared to the group that received no stimulation.

It should be appreciated that a variety of different cell types may be used in connection with the electrically conductive hyaluronic acid-based hydrogel 2. This includes not only NS/PCs but other stem cells, immortalized human progenitor cells, and the like. The cells may be patient-derived, from another patient or mammal, or synthetically derived. As explained herein, in some embodiments, the electrically conductive hyaluronic acid-based hydrogel 2 is loaded with or seeded with cells ex-vivo which are then delivered to the body. The electrically conductive hyaluronic acid-based hydrogel 2 may also recruit, promote, and promote infiltration of the patient's own endogenous cells. In some embodiments, cells loaded or seeded in or on the electrically conductive hyaluronic acid-based hydrogel 2 may beneficially increase the growth and infiltration of native cells from the surrounding tissue at the site of implantation or delivery.

The following illustrates various ways in which the electrically conductive hyaluronic acid-based hydrogels 2 may be made.

Figure 5B:
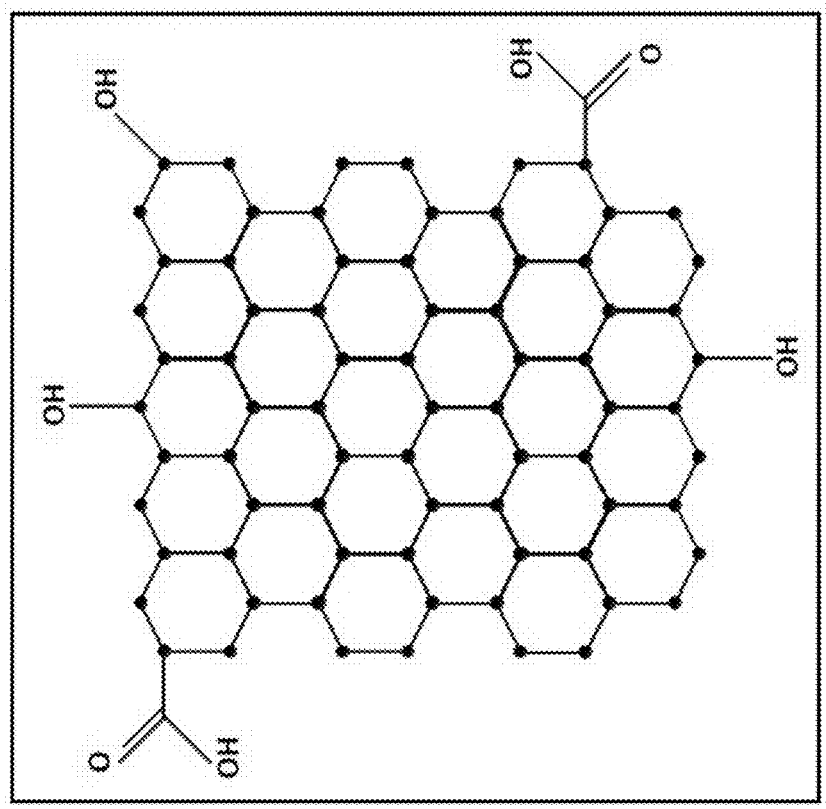
FIG. 5B illustrates the chemical structure of reduced graphene oxide.
Figure 5A:
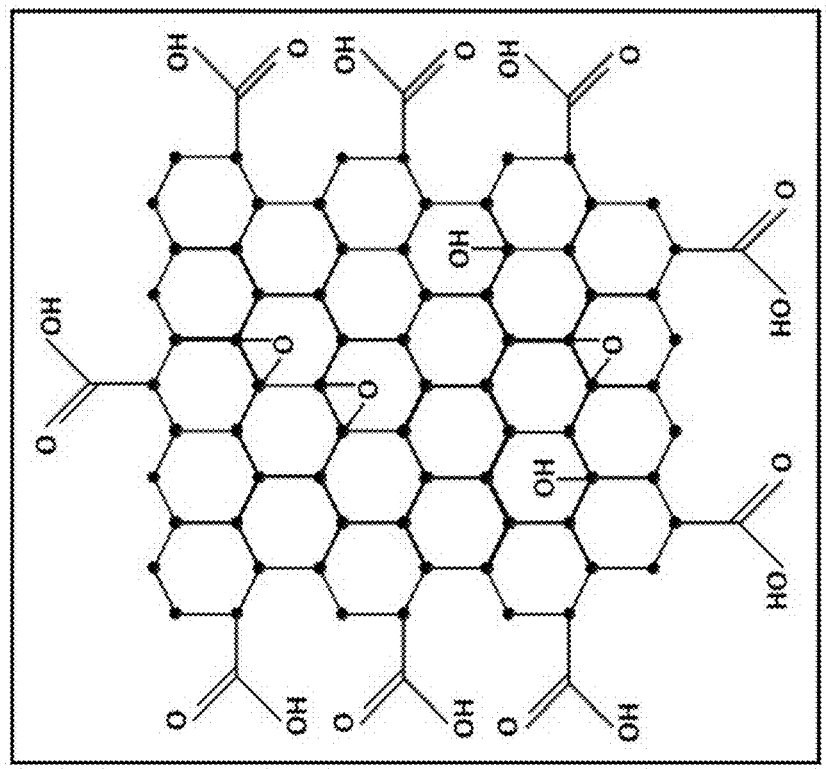
FIG. 5A illustrates the chemical structure of graphene oxide.

Graphene Oxide (GO): First graphene oxide is prepared through a liquid-phase exfoliation process modified from Hummers and Offeman. See Hummers, W. S., & Offeman, R. E., Preparation of Graphitic Oxide. *Journal of the American Chemical Society*, 80(6), 1339 (1958), which is incorporated herein by reference. The process starts with powdered graphite flakes that are combined at a 2:1 ratio with sodium nitrate into 66° Be technical grade sulfuric acid. While not exceeding a temperature of 20° C. and stirring continuously on a magnetic stir plate, potassium permanganate is added. Then the solution is brought to 35° C. and maintained for 30 minutes. At this point deionized water (DI $H_2O$) is added, the temperature is raised to 90° C. and the suspension is stirred for another 30 minutes. Next, 3% hydrogen peroxide is added, and the solution is left until a color change to yellow occurs and no more gas is produced. The suspension is then filtered and washed several times with 5% hydrochloric acid, filtered again and rinsed several times with DI $H_2O$ to remove residual acid. This reaction is maintained at a warm temperature to avoid precipitation. A filter cake remains, which is then dried in air and dispersed in deionized water through sonication to obtain a GO suspension. FIG. 5A illustrates the chemical structure of graphene oxide and FIG. 5B illustrates the chemical structure of reduced graphene oxide.

Figure 6B:
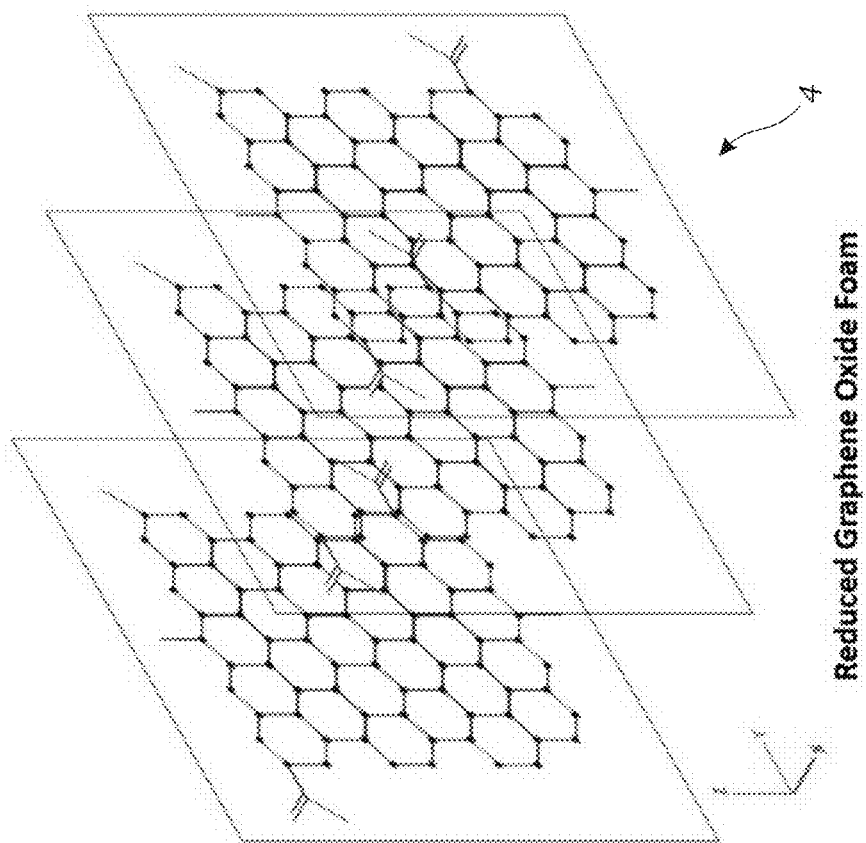
FIG. 6B illustrates a representation of reduced 3D graphene oxide foam.
Figure 6A:
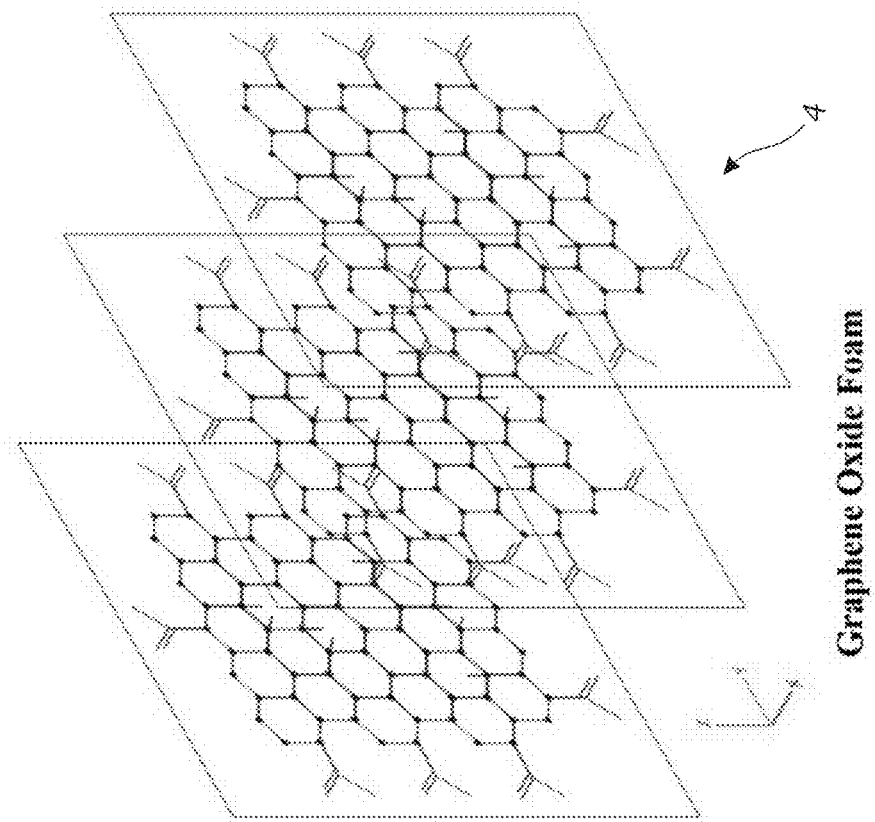
FIG. 6A illustrates a representation of 3D graphene oxide foam.

Graphene Oxide Foam (GO Foam): To make GO foam, the GO suspension is then pipetted into a 15 mL conical tube that is kept upright in a Styrofoam tube rack leaving the bottom of the tube non-insulated to contact with a liquid nitrogen bath. The GO/DI $H_2O$ solution is then lyophilized for 48 hours and stored in a desiccator. For experiments that require cell culture, a batch (5 aliquots) of GO foam is then set aside to undergo a sterilization process which involves rinsing with 70% ethanol for 12 hours, diluting the solution to 30% ethanol with sterile DI $H_2O$ and then lyophilizing for 48 hours. Aliquots are then sealed in a Biosafety Cabinet (BSC), vacuum packaged and stored at −20° C. until use. FIG. 6A illustrates schematically the 3D nature of GO foam.

Reduced Graphene Oxide Foam (rGO Foam): To make rGO foam, the GO foam can be thermally reduced by placing the lyophilized GO foam in a Na atmosphere oven for an hour at 100° C., another hour at 150° C. and then two hours at 200° C. FIG. 6B illustrates schematically the 3D nature of rGO foam. For experiments that require cell culture, a batch (5 aliquots) of rGO foam is then set aside to undergo a sterilization process which involves rinsing with 70% ethanol for 12 hours, diluting the solution to 30% ethanol with sterile DI $H_2O$ and then lyophilizing for 48 hours. Aliquots are then sealed in a BSC, vacuum packaged and stored at −20° C. until use.

Electrically conductive hyaluronic acid-based hydrogel (HA-SH): Next is the process of incorporating the graphene-based material 4 (e.g., rGO foam) into hyaluronic acid-based hydrogels (HA-SH). Silicone rubber molds (4.5 mm diameter by 2 mm deep, 80 µL volume, Grace BioLabs) are first autoclaved, then cooled, dried and placed into the bottom of 24-well plates. Stock solutions of 100 mg/mL 20 kDa 4-arm PEG-Mal (Laysan Bio, Inc), 150 mg/mL 20 kDa 4-arm PEG-SH (Laysan Bio, Inc) and 4 mM RGD containing peptide (GCGYGRGDSPG) (Sigma-Aldrich) are then prepared. RGD is a cell adhesion peptide and other cell adhesion peptides may be used. Thiolated hyaluronic acid (HA-SH) is placed in a brown vial, weighed, covered with aluminum foil and labeled. A small magnetic stir bar is added as well as HEPES buffer (20 mM, pH 7) at a specific starting concentration (15 mg/mL) (other concentrations may also be used). The vial is then placed on a magnetic stir plate and left to dissolve. Meanwhile, the cross-linker solution (PEG-Mal, RGD and PBS) is prepared so that RGD is conjugated to about 12.5% of the maleimide groups of the PEG-Mal. Then 0.01-1.0 (w/v %) rGO foam is added to this solution, vortexed to mix and left for 30 minutes at room temperature. This will encapsulate the rGO foam within the HA-based hydrogel (e.g., FIG. 1). Note, however, that higher concentrations of rGO foam may be used as explained herein (e.g., up to at least 3.8% w/v). Alternatively, a more specific binding method would entail replacing 4-arm PEG-Mal with Mal-PEG-Amine (Nanocs, Inc) and through EDC/NHS chemistry utilizing the edge carboxylic acid groups of the GO/rGO foam to conjugate to the amine of the PEG, crosslinking it to the HA-based hydrogel.

After the HA-SH solution dissolves, it is transferred to a 2 mL microcentrifuge tube and diluted to its final concentration (10 mg/mL). This dilution is accomplished using PEG-SH and PBS to create the pre-calculated solution. This mixture is then pH adjusted to a biological pH (7-7.5) and placed on ice. Next 40 μL of HA-SH solution is added to each silicone mold with a wide-bore pipette tip. Then 40 μL of the cross-linker/rGO Foam solution is added to each mold and the solution is pipetted and stirred quickly. Hydrogels are cross-linked via Michael-type Addition (FIG. 3) resulting in a 0.5 (w/v %) HA concentration and 1:1.2 ratio of total thiol to maleimide. The well plate is placed in a bead bath (37° C.) for 30 minutes to allow the hydrogels to fully form. The silicone molds are then carefully removed, leaving the hydrogels within the wells. PBS (1 mL) is added to each well, then the well plate is wrapped with Parafilm and stored at 4° C. overnight. For experiments involving cell culture a similar experimental design is employed with a few changes. 20 μL silicone molds are used in a 48-well plate instead of 80 silicone molds in a 24-well plate. All chemicals are kept sterile and the procedure is performed in the BSC. Media is added to each well after hydrogel crosslinking instead of PBS and the well plate of hydrogels is transferred to an incubator (37° C. 5% $CO_2$ 95% humidity). Typically, 200 k NS/PCs are encapsulated into each 20 μL HA-based or Graph-HA-based hydrogel.

Electrically Conductive Hyaluronic Acid-Based Hydrogel (MeHA):

MeHA was dissolved in 20 mM pH 7 HEPES buffered solution and combined with thiol-terminated 4-arm polyethylene glycol (PEG-SH, 20 kDa, Laysan Bio), norbornene-terminated 8-arm polyethylene glycol (PEG-Norb, 20 kDa, JenKem Technology), an RGD containing peptide (GCGYGRGDSPG), and lithium phenyl-2,4,6-trimethylbenzoylphosphinate (LAP) forming the HA solution. Reduced graphene oxide foam (rGO, Kaner Lab UCLA), graphene oxide foam (GO, Kaner Lab UCLA), or graphene nanoplatelets (GNPs, Tokyo Chemical Industry Co., G0441) was dissolved in a 20 mM pH 7 HEPES buffered solution to form the graphene solution. Hydrogel solutions were then made by combining the HA and graphene solutions and adjusting the pH to about 7. Silicone rubber molds (4.5 mm diameter by 2 mm deep, 80 μL volume, Grace BioLabs) were autoclaved, cooled, dried and placed individually onto glass slides. Hydrogel solution (80 μL each) was added to one mold at a time and exposed to UV irradiation (~4 mW/cm$^2$) for one minute to form the gels according to a photoinitiated thiol-ene reaction. The silicone rubber molds were then carefully removed, and the hydrogels were moved into a 24-well plate where PBS (1 mL) was added to each well. Then the well plate was wrapped with Parafilm and stored at 4° C. until testing. Note that MeHA hydrogel fabrication was limited to at most 0.5% (w/v) of graphene-based material 4. Above this limit led to reduced photocrosslinking of the hydrogels. In contrast, there was no observed limit for HA-HA hydrogel fabrication and as much as 3.8% (w/v) has been tested.

Alternative methods for the incorporation of graphene-based materials 4 into the hyaluronic acid-based hydrogel 2 are numerous. Two specific alternatives include electrospun graphene oxide fibers and a multi-layered substrate composed of reduced graphene oxide nanoplatelets.

Electrospun Graphene Oxide Fibers (GO Fibers): An alternative method to incorporate graphene-based material 4 into the hyaluronic acid-based hydrogel 2 is to first create an electrospun scaffold of graphene oxide-poly(ε-caprolactone) (GO-PCL) that can then be encapsulated into the hydrogel 2 (FIG. 7C), used as a substrate beneath the hyaluronic acid-based hydrogel 2 (FIG. 7D), coated onto the microelectrode array (e.g., FIG. 9B) or structured as conductive regions within the hydrogel 2 located above the actual metal electrodes 102 of a microelectrode array 100 (FIG. 10B). To make this particular embodiment of the hyaluronic acid-based hydrogel 2, graphene nanoplatelets (Tokyo Chemical Industry—Catalog—G0441) and poly(ε-caprolactone) (PCL) (Mol wt 65,000 g/mol) are obtained. The Graphene nanoplatelets are then modified into Graphene Oxide nanoplatelets (GO nPs) via the Hummers method mentioned supra. A solution of PCL (1 mg/25 mL) and GO (10 μg/mL) is combined with chloroform in a 200 mL glass bottle and sonicated over a one-hour period. This solution is then loaded into a 10 mL syringe with a 14-gauge needle and attached to an electrospinning machine in which the needle is connected to a high voltage supply (~15 kV). The flow rate of the solution is then adjusted to 1.5 mL/hour and the fibers are collected onto a mandrel located about 12 cm from the needle setup. An example of how such fibers are collected using the needle setup may be seen in Chaudhuri, B. et al., Biocompatibility of electrospun graphene oxide-poly (ε-caprolactone) fibrous scaffolds with human cord blood mesenchymal stem cells derived skeletal myoblast, *Materials Letters*, 126, 109-112 (2014) which is incorporated by reference herein. Next the GO-PCL electrospun scaffold is removed from the mandrel and sterilized under Ultraviolet (UV) radiation at a wavelength between 240-280 nm for 20 minutes. The sterile GO-PCL scaffold is then either rolled into cylinders (0.25 mm diameter×0.2 mm) or cut into small pieces (0.5 mm×0.2 mm×0.2 mm) in the BSC. These are then utilized in the aforementioned manner.

Layer Deposited Reduced Graphene Oxide Nanoplatelets (rGO nPs): Graphene nanoplatelets are obtained (Tokyo Chemical Industry—G0441) and modified into GO nPs via the Hummers method mentioned supra. To produce reduced Graphene Oxide nanoplatelets (rGO nPs), the following method is employed. First, GO nPs are combined with a solvent (9:1 DMF/water) at a 5:1 ratio within a four-necked flask, stirred and ultrasonicated for half an hour. Next, 0.025 g of $NaBH_4$ is added to the mixture and the solution is heated to 80° C. for four hours. Once rGO nPs are observed, acrylic acid solution in $H_2O$ (10 g/40 mL) is added to the flask and stirred for half an hour at which time oxygen is removed by purging with dry nitrogen for half an hour. $(NH_4)_2S_2O_8$ solution in $H_2O$ (100 mg/80 mL) is then added using a dropping funnel and the solution is placed in an oil bath (60° C.) for 48 hours at which time it is cooled to 23° C., diluted in 200 mL of $H_2O$, sonicated for one hour and centrifuged. Now the rGO nPs can be assembled into layer-by-layer (LBL) films. First, glass slides are treated to form a hydrophilic coating. Concentrated $H_2SO_4$ and $HNO_3$ (3:1 v/v %) is applied followed by several rinsing steps with doubly distilled $H_2O$. Next, a positively charge solution of PDDA (1 mg/mL with 0.5M NaCl), negatively charged solution of PAA-g-graphene (0.1 mg/mL), positively charged solution of PAM-g-graphene (0.1 mg/mL with HCl to obtain pH=3 and protonation) and a negatively charged solution of PAAS (1 mg/mL with 0.5M NaCl) are prepared. Then the glass slides undergo cyclic immersion carried out in open beakers within a BSC at room temperature. The process is structured as immersion cycles in (PDDA/PAA-g-graphene/PAM-g-graphene/PAAS) for the number of desired layers. In between each cycle, distilled water is used to rinse the slides several times and they are dried with bubbling nitrogen. Details regarding layer-by-layer assembly of graphene nanoplatelets may be found in Li, C. et al., Layer-by-Layer Self-Assembly of Graphene Nanoplatelets. *Langmuir,* 25(11), 6122-6128, (2009), which is incorporated herein by reference.

Once the LBL assembly is complete, these layers can be used as a highly conductive scaffold on which to make the hyaluronic acid-based hydrogels 2 (FIG. 7D) or as a conductive filler within apertures/holes of the hyaluronic acid-based hydrogel 2 coating of the microelectrode array 100 (FIG. 10). The conductive filler may also include the rGO foam or the electrospun GO fibers that are described herein. The graphene-based material 4 that fills the apertures/holes 104 may be combined with an electrically conductive epoxy (e.g., silver epoxy) in some embodiments.

The first technique allows for in vitro testing of encapsulated NS/PCs within the hyaluronic acid-based hydrogels 2 in which stimulation schemes can be applied through the glass slide electrode/hydrogel contact to assess functional neuronal network formation.

Since one of the goals of this novel hydrogel is to be applied as a conductive, biomimetic coating for a microelectrode array, a method for conjugating the hydrogel to a polyimide-based array is described next. Polyimide can be functionalized to have amine-thiol crosslinks on its surface. This allows for thiol click chemistry between the microelectrode array and the Graph-HA hydrogel coating, leaving the platinum/iridium electrodes exposed for further treatment with a graphene-based substrate as described below. Once the microelectrode array has been functionalized, the Graph-HA hydrogel coating can be applied through a dip coating technique, spray coating, or painting the coating onto the microelectrode array. (FIG. 8). While crosslinking described herein does not use photocrosslinking, in other embodiments, Graph-HA hydrogel may be made using photocrosslinking via PEG-Norbornene and a photo initiator, such as Lithium phenyl-2,4,6-trimethylbenzoylphosphinate (LAP), under UV irradiation.

In one embodiment, the Graph-HA hydrogel has chemical and mechanical properties closely matched to that of the native spinal environment. The HA concentration should generally be around 0.5 (w/v %) and target stiffness (complex modulus) within the range of 150-400 Pascals (as measured using a rheometer). For applications that use the Graph-HA hydrogel with a microelectrode array, a conductance of at least a magnitude greater than that of native CSF (0.018 S/cm) should be achieved. For example, a target conductance at around 0.1 to 10 S/cm is preferred. This will allow for the transmission of electrical signal from the microelectrode array through the hydrogel coating to the spinal cord without significant loss of signal to surrounding areas. Conductance may be measured using either Electrical Impedance Spectroscopy or Cyclic Voltammetry and conductivity will be calculated based on hydrogel geometry and electrode separation distance.

While embodiments of the present invention have been shown and described, various modifications may be made without departing from the scope of the present invention. The invention, therefore, should not be limited, except to the following claims, and their equivalents.

What is claimed is:

1. An implantable bioelectronic device comprising a plurality of electrodes, the device comprising a polymer coated body and a plurality of metallic electrodes, wherein an electrically conductive hyaluronic acid-based hydrogel crosslinked into a porous scaffold is adhered to the polymer coated body and wherein the crosslinked porous scaffold is punctuated with holes or apertures located adjacent to the plurality of metallic electrodes, wherein the holes or apertures contain a graphene-based material therein.

2. The implantable bioelectronic device of claim 1, wherein the porous scaffold is formed by thiolated hyaluronic acid chains (HA-SH), multi-arm polyethylene glycol (PEG) thiol (PEG-SH), and multi-arm polyethylene glycol maleimide (PEG-Mal).

3. The implantable bioelectronic device of claim 1, wherein the porous scaffold is formed by methacrylated hyaluronic acid chains (MeHA), multi-arm polyethylene glycol (PEG) thiol (PEG-SH), and multi-arm polyethylene glycol norbornene (PEG-Norb).

4. The implantable bioelectronic device of claim 1, further comprising one or more of: a peptide, a protein or fragment thereof, a cell adhesion peptide, or a therapeutic drug disposed on or within the crosslinked porous scaffold.

5. The implantable bioelectronic device of claim 1, wherein the graphene-based material comprises graphene oxide foam or reduced graphene oxide foam.

6. The implantable bioelectronic device of claim 1, wherein the graphene comprises a graphene oxide poly(ε-caprolactone) (GO-PCL) scaffold or fibers in contact with the crosslinked porous scaffold.

7. The implantable bioelectronic device of claim 1, wherein the graphene-based material is reduced.

* * * * *